United States Patent [19]

Kropp

[11] Patent Number: 5,086,652
[45] Date of Patent: Feb. 11, 1992

[54] MULTIPLE PAD CONTACT SENSOR AND METHOD FOR MEASURING CONTACT FORCES AT A PLURALITY OF SEPARATE LOCATIONS

[75] Inventor: Harry C. Kropp, Chicago, Ill.

[73] Assignee: Fel-Pro Incorporated, Skokie, Ill.

[21] Appl. No.: 660,703

[22] Filed: Feb. 25, 1991

[51] Int. Cl.[5] .................................. G01B 7/18
[52] U.S. Cl. ............................. 73/767; 73/862.38
[58] Field of Search .......... 73/767, 772, 774, 862.38

[56] References Cited

U.S. PATENT DOCUMENTS

| | | | |
|---|---|---|---|
| 4,734,034 | 3/1988 | Maness et al. | 433/68 |
| 4,856,993 | 8/1989 | Maness et al. | 433/68 |

FOREIGN PATENT DOCUMENTS 182746 10/1983 Japan ..................... 73/774

Primary Examiner—Jerry W. Myracle
Attorney, Agent, or Firm—Dressler, Goldsmith, Shore, Sutker & Milnamow, Ltd.

[57] ABSTRACT

A contact sensor formed of a pair of thin flexible insulating sheets and having a plurality of elongate flexible leads, each connected to a single terminal and having an independent sensing pad positionable via the elongate flexible leads at separate selected locations between a pair of confronting surfaces to separately and independently sense the loads applied at the separate selected locations.

5 Claims, 4 Drawing Sheets

MULTIPLE PAD CONTACT SENSOR AND METHOD FOR MEASURING CONTACT FORCES AT A PLURALITY OF SEPARATE LOCATIONS

BACKGROUND OF THE INVENTION

Contact sensors for sensing and measuring opposing forces at a plurality of locations, and systems for using them are disclosed in U.S. Pat. Nos. 4,734,034 and 4,856,993. Such sensors broadly comprise a pair of backing sheets, each with a set of parallel electrodes, with the sets of parallel electrodes in a facing, crossing pattern, thereby providing a plurality of closely adjacent intersections A resistive, semi-conductive material is disposed between the facing electrodes at each intersection. As such a variable output from the sensor depending upon the relative force applied may be obtained at each intersection. Typical materials used to form such sensors, their dimensions, the associated connectors or reader heads, etc., are all described in the above-identified patents, the disclosures and content of which are here incorporated by reference.

There are many environments in which it would be desirable to use contact sensors to detect the forces applied to confronting surfaces, the uniformity or lack of uniformity of the application of forces in different zones of the confronting surfaces and the like. In many instances such surfaces have obstructions associated with them which makes it impossible to use a single sensor with a single connector, requiring the use of multiple sensors and multiple connectors. This is both exceedingly expensive and inconvenient, and sometimes, because of space limitations, almost impossible to accomplish.

As such a more universal contact sensor usable with a single reader or connector would be desirable.

SUMMARY OF THE INVENTION

In accordance with the present invention an improved contact sensor having a plurality of sensing pads insertable between a pair of confronting surfaces to sense the loads applied at each of a plurality of selected locations, and usable with a single connector/reader is provided.

The contact sensor comprises a pair of thin flexible insulating sheets secured to each other in a confronting relationship and including a single terminal, a plurality of elongate flexible leads extending from said terminal, each lead being separately flexible, and an independent sensing pad at the remote end of each lead. Each of the sensing pads has a first set of electrodes on one of the sheets and a second set of electrodes on the other of the sheets in a crossing relationship to the first set of electrodes. Pressuresensitive resistive material is disposed between the sets of electrodes in the zones of their crossing relationships. The sets of electrodes define plural intersections in each of the sensing pads.

The terminal has a plurality of contacts which are adapted to be received in a single connector having complementary contactors for receiving signals from the plurality of contacts. The conductors extend from each of the electrodes along the leads to the terminal. Each of the sensing pads is separately and independently positionable via the separately flexible leads in a separate selected location between a pair of confronting surfaces to sense the loads applied at each of the selected locations.

Further objects, features and advantages of the present invention will become apparent from the following description and appended drawings.

DESCRIPTION OF A PRESENTLY PREFERRED EMBODIMENT OF THE INVENTION

Figure 1:
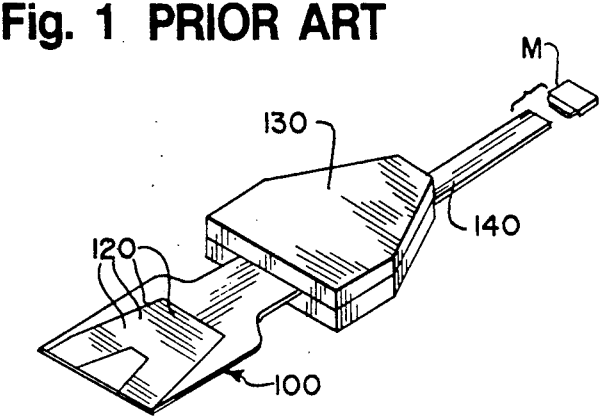
FIG. 1 illustrates a prior art contact sensor and a device for reading outputs therefrom.

A typical contact sensor 100 made in accordance with the prior art as typically described in U.S. Pat. No. 4,856,993 is schematically illustrated in FIGS. 1-4. Thus, the sensor 100 includes a first thin flexible backing sheet 102 on which a first plurality of parallel electrodes 104 are deposited and a second thin flexible backing sheet 110 on which a plurality of electrodes 112 are deposited in a pattern to cross electrodes 104, thereby to provide a large plurality of intersections 120. The backing sheets may be of a polyester film such as Mylar.

Figure 3:
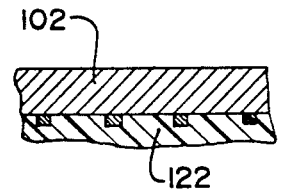
FIGS. 3 and 4 are fragmentary cross-sectional views of the prior art contact sensor of FIG. 1.
Figure 2:
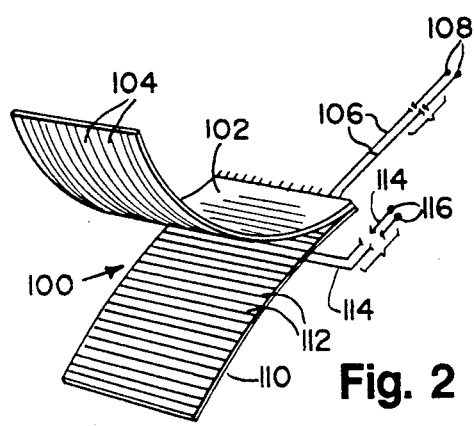
FIG. 2 is a schematic view of a portion of a prior art contact sensor of FIG. 1.
Figure 4:
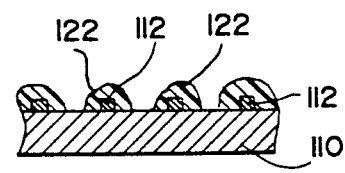
Figure 5:
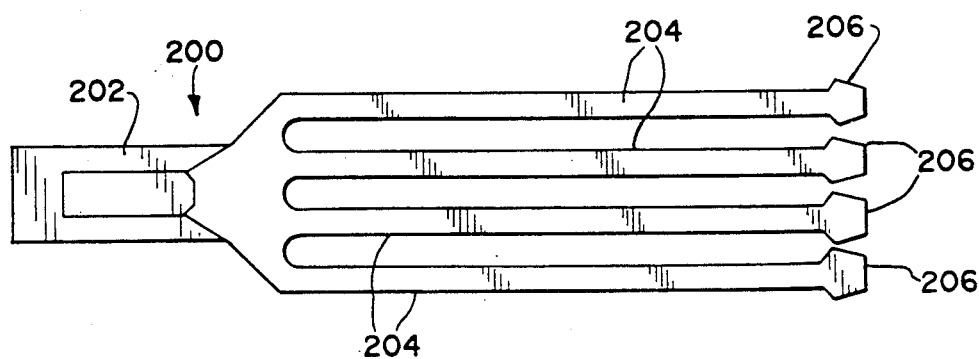
FIG. 5 is a plan view in outline of a contact sensor of the present invention.
Figure 6:
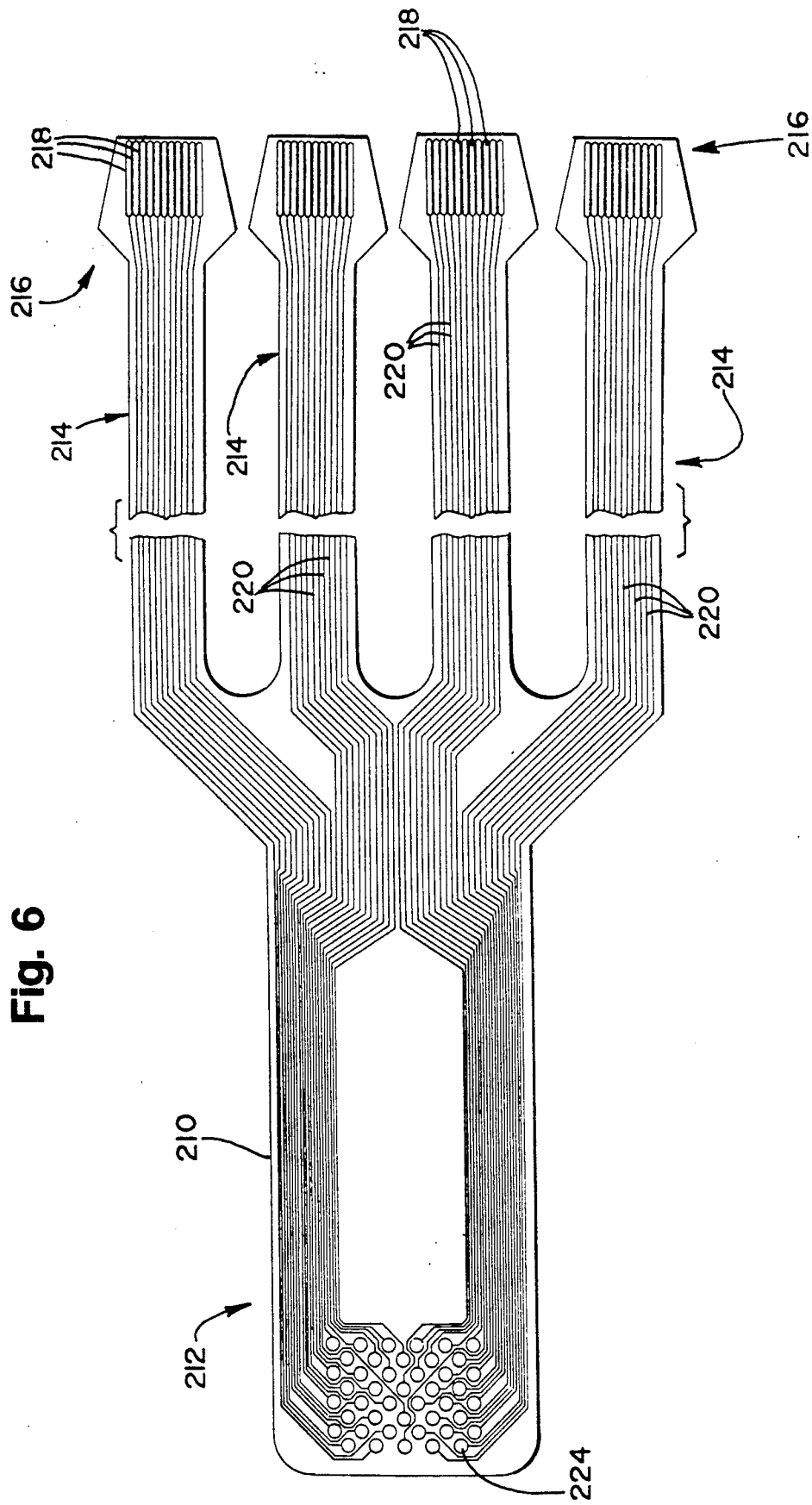
FIG. 6 is an enlarged view of a top layer of the contact sensor.

As seen in FIGS. 3 and 4 the electrodes 104 are coated with a resistive material 122 whereas the electrodes 112 may be coated with stripes of a resistive material 122. Preferably the resistive material may be a carbon-molybdenum disulfide material in an acrylic binder, which material has variable force versus electrical resistance characteristics obtainable with contact sensors of this type. Except under pressure, the crossing electrodes are electrically isolated at the intersections by the resistive material.

Each electrode 104, 110 is connected to a lead or conductor 106, 114, respectively, which terminates in a contact 108, 116, respectively. The contacts 108, 116 are positionable in a reader or connector 130 which in turn is connected to a multi-conductor cable 140 for the measurement electronics, microprocessor M, all as disclosed in U.S. Pat. No. 4,856,993.

The connector 130 receives the signals from the electrodes via the conductors 106, 114 and the contacts 108, 116 on the sensor 100. The contacts are in direct electrical contact with corresponding contacts in the connector, and as such the signals produced by force applied at various of the intersections are directly transmitted via cable 140 to the microprocessor M.

In accordance with the present invention a single read head or connector, such as connector 130, may be used to transmit signals produced by forces applied at a plurality of discrete locations to a multiple pad contact sensor 200, in a manner like that in U.S. Pat. No. 4,856,993.

Referring now to FIGS. 5 to 8, a contact sensor 200 is seen to include a first or top flexible layer 210, as of a Mylar polyester, and a flexible second or bottom layer 250, as of a Mylar polyester. Top layer 210 comprises a terminal portion 212 and a plurality of elongated flexible lead portions 214. Each lead portion 214 terminates in a sensing pad portion 216. Each sensing pad portion 216 carries a plurality of electrodes 218 which are disposed in parallel rows. Each electrode 218 is connected by a conductive trace such as a conductor 220 which extends from an electrode 218 along a lead portion 214 to the terminal portion 212 where it terminates in a contact 224.

Figure 7:
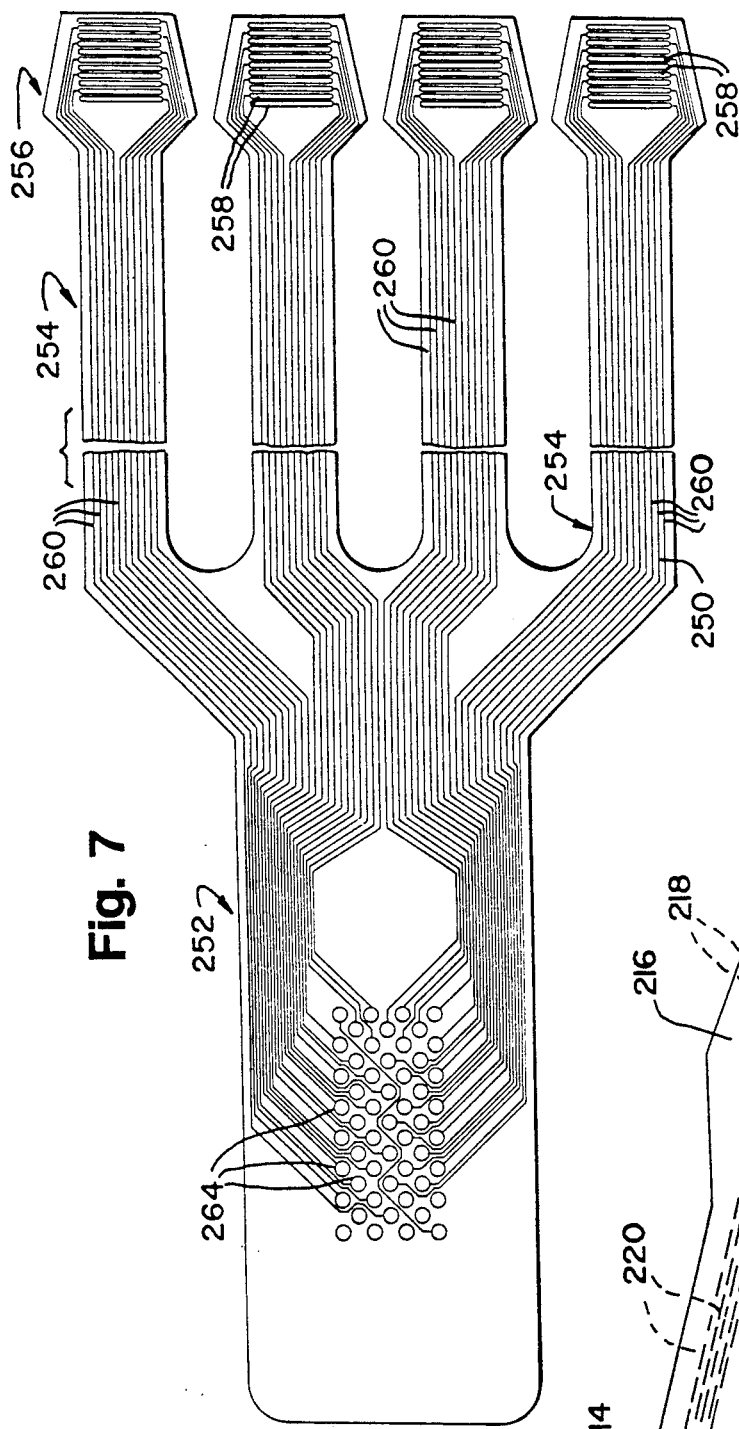
FIG. 7 is an enlarged view of a bottom layer of the contact sensor of FIG. 9.
Figure 8:
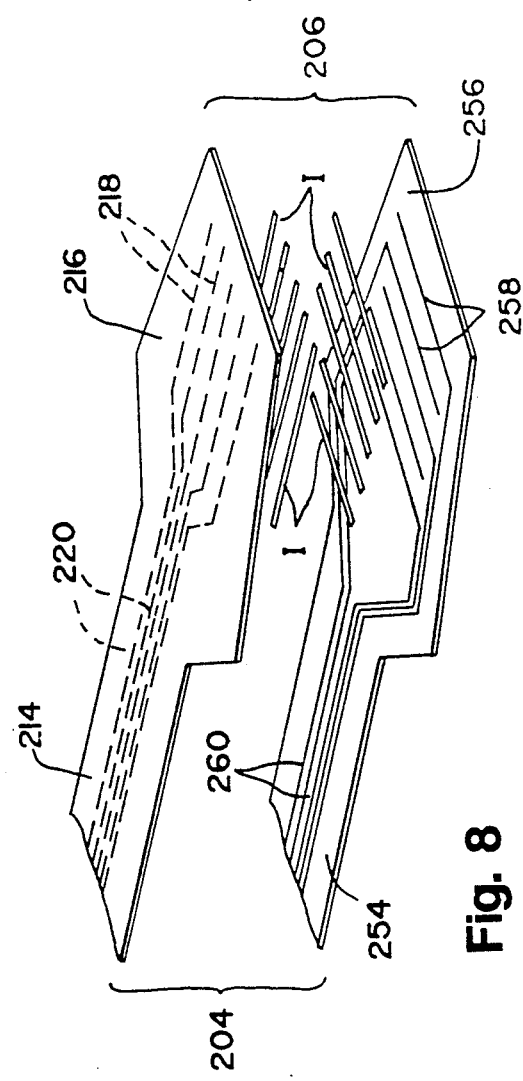
FIG. 8 is an exploded perspective view representative of a sensor pad of the contact sensor of FIGS. 6 and 7.

As seen in FIG. 7, bottom layer 250 includes a terminal portion 252 and a plurality of elongated flexible lead sections 254. Each lead section terminates in a sensing pad portion 256 which carries a plurality of electrodes 258. Electrodes 258 are disposed in parallel rows on the section 256. Each electrode 258 is connected via a conductor 260 extending from the electrode along a lead portion to the terminal portion 252 where it terminates in a contact 264. It is apparent that the electrodes 218, 258 for each pad are mechanically and electrically separate from and independent of the electrodes 218, 258 of each other sensing pad.

Layers 210 and 250 are of thin flexible material and are provided with the associated conductors and electrodes via an electrically conductive ink deposited as by a screen printing process. The electrodes 218 and 258 which are in a crossing relationship are provided with a covering of a pressure sensitive resistive ink I, as in the manner described in U.S. Pat. No. 4,856,993. The conductors are covered with an electrically insulative material so that the conductors are electrically insulated from each other, again as described in U.S. Pat. 4,856,993.

Thus, when top layer 210 and bottom layer 250 are superimposed and adhered to each other, forces applied to the sensing pads 206 formed of sensing sections 216, 256 will produce signals representative of changes in electrical resistance which are conducted via conductors 220 and 260 to the terminal which is formed of terminal portions 212, 252. The associated contacts 224, 264, when disposed in an appropriately configured connector having aligned contactors will provide signals from the conductors for transmission to the microprocessor M for sensing and reading in the manner described in U.S. Pat. No. 4,856,993.

A typical contact sensor of the configuration illustrated in FIGS. 5–8 has lead portions 214, 254 about 10 inches in length and about ½ inch wide with pads about ⅞"×⅞" at their widest points. The terminal together with the portions from which the leads neck down to the terminal may be about 5¼ inches in length.

The elongated leads formed from lead portions 214, 254 are also flexible. Accordingly, their associated sensing pads may be positioned at varying orientations relative to each other for the sensing of loads applied at a plurality of locations which are of interest. With the plurality of sensing pads, these locations may be separate, need not be co-planar, and may otherwise be out of alignment because of obstructions, such as bolt holes, or the like. They might not otherwise be readable because creases or sharp bends in the contact sensor, such as in the leads, would otherwise occur. Yet all the locations at which the applied pressure may be of interest may be sensed simultaneously via a single connector without interference by one sensing pad with another.

Figure 9:
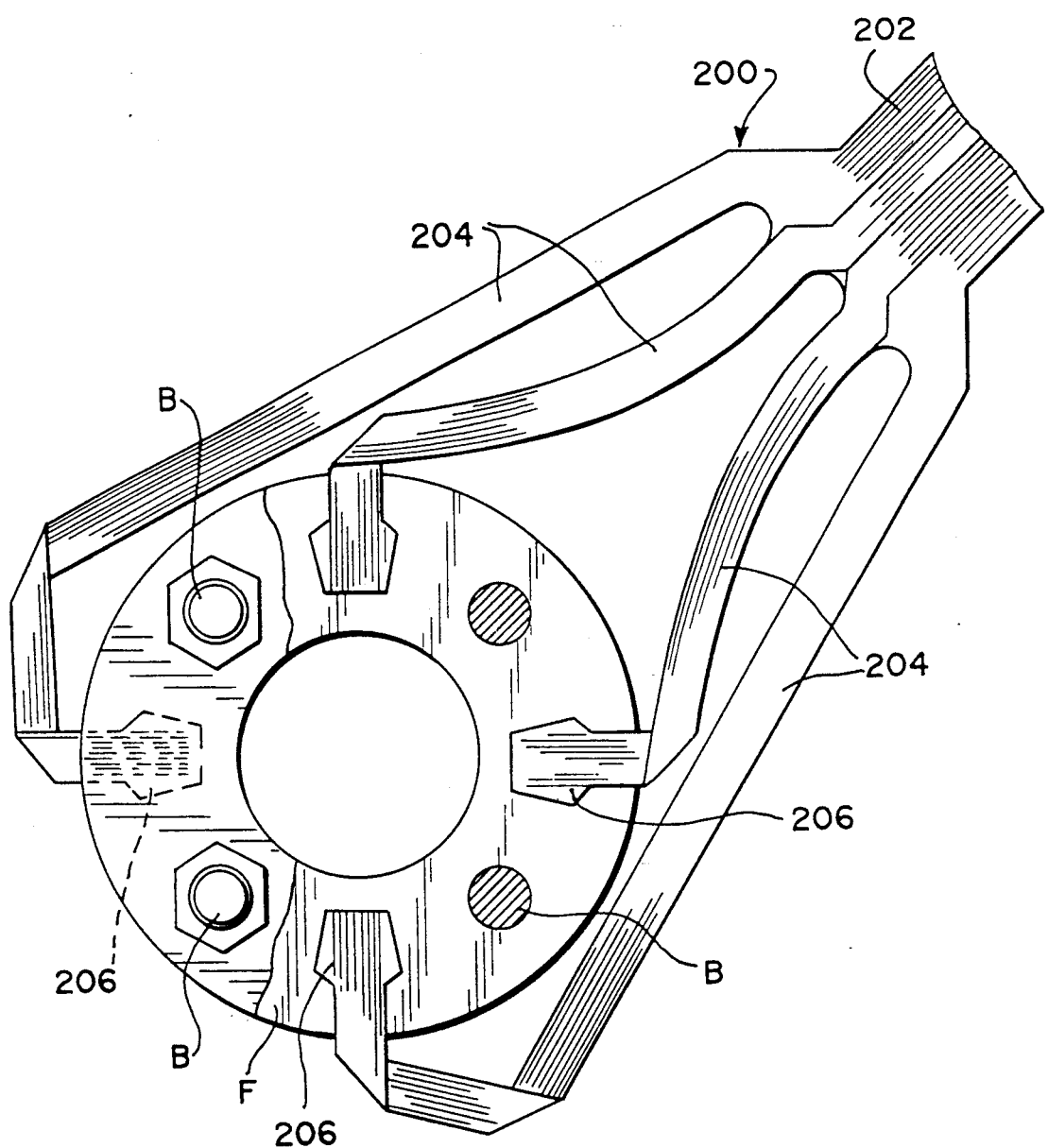
FIG. 9 illustrates a typical environment in which a contact sensor of FIGS. 5-8 may be conveniently used.

FIG. 9 illustrates a typical environment in which a contact sensor of FIGS. 5–8 may be conveniently used. The contact sensor 200 is positioned with its terminal accessible to a single connector reader and with its four sensing pads in selected locations in a joint, as between a pair of flanges F which are to be sealed against each other by four bolts B. As the torquing proceeds, the forces applied at the four locations at which sensing pads 206 are positioned may be monitored simultaneously, for example to make certain that the flanges are in compression with equal forces at all locations around the confronting surfaces. The flexibility of the elongate leads 204 makes it possible and convenient to utilize a single contact sensor and a single connector for determining the loads applied and/or their uniformity around the joint, something which is simply not possible with contact sensors as illustrated in the patents referred to above.

Thus the multi-pad contact sensor having plural separate elongate leads for the sensing pads provides a sensor assembly which is highly flexible in use may be used to secure force information from multiple areas in which the prior art contact sensors could not be used.

From the foregoing it will be apparent to those skilled in the art that other fixtures and methods of using same may be devised without departing from the spirit and scope of the invention. As such it is intended that the invention is not to be construed as being limited thereby.

What is claimed is:

1. A contact sensor comprising a pair of thin flexible insulating sheets secured to each other in a confronting relationship and including a single terminal, a plurality of elongate flexible leads extending from said terminal, each said lead being separately flexible, and a sensing pad at the remote end of each lead, each of said sensing pads having a first set of electrodes on one of said sheets and a second set of electrodes on the other of said sheets in a crossing relationship to said first set of electrodes, and pressure-sensitive resistive material disposed between said sets of electrodes in the zones of their crossing relationships, said sets of electrodes defining plural intersections in each of said sensing pads, said terminal having a plurality of contacts and adapted to be received in a single connector having complementary contactors for receiving signals from said plurality of contacts, and conductors extending from each of said electrodes along said leads to said terminal, and each of said sensing pads being separately positionable via said separately flexible leads in separate selected locations between a pair of confronting surfaces to sense the loads applied at each said selected location.

2. A method of sensing loads applied by a pair of confronting surfaces at a plurality of discrete selected locations between them and sensing the loads via a single connector, comprising the steps of:

providing a contact sensor comprising a pair of thin flexible insulating sheets secured to each other in a confronting relationship and having a single terminal, a plurality of elongate flexible leads extending from said terminal, each said lead being separately flexible, and a sensing pad at the remote end of each lead, each of said sensing pads having a first set of electrodes on one of said sheets and a second set of electrodes on the other of said sheets in a crossing relationship to said first set of electrodes, to define plural intersections in each of said sensing pads, and pressure-sensitive resistive material disposed between said sets of electrodes in the zones of said intersections, said terminal having a plurality of contacts and adapted to be received in a single connector having complementary contactors for receiving signals from said plurality of contacts, and conductors extending from each of said electrodes along said leads to said terminal;

separately positioning each of said sensing pads via said separately flexible leads in separate selected locations between a pair of confronting surfaces;

compressing the confronting surfaces to compress the sensing pads between them; and simultaneously sensing the loads at each of said locations.

3. A contact sensor comprising:

a pair of thin, flexible insulating sheets secured to each other in confronting relationship to define a single terminal portion, a plurality of elongate flexible lead portions extending from said terminal portion and being separately flexible, each of said lead portions terminating in a sensing pad portion at the remote end thereof;

each of said plurality of sensing pad portions comprising independent sensing pads, each being separately positionable generally independently of the others in separate selected locations between pairs of confronting surfaces to sense the load applied thereto at each of said selected locations;

each of said independent sensing pads having a first set of electrodes on one of said sheets, and a second set of electrodes on the other of said sheets in a crossing relationship to said first set of electrodes to define a plurality of intersections in each of said sensing pads, said first and second sets of electrodes for each of said sensing pads being mechanically and electrically separate from and independent of said first and second sets of electrodes, respectively, for each of the other sensing pads, said sensing pads further including pressure-sensitive resistive material disposed between said sets of electrodes in the zones of said intersections;

said terminal having a plurality of contacts and being adapted to be received in a single connector having complementary contactors for electrical connection to said plurality of contacts to apply and receive signals from selected ones thereof; and a plurality of flexible conductors extending from each of said sets of electrodes for each of said sensing pads along said flexible leads to separate contacts in said terminal.

4. A contact sensor as claimed in claim 3 wherein each of said sensing pad are capable of being oriented in positions and at angles different from each of the other sensing pads.

5. A contact sensor as claimed in claim 3 wherein loads applied at any one of said locations and being sensed by one of said sensing pads are sensed simultaneously with the sensing of a load by another of said sensing pads without interference therebetween.

* * * * *